United States Patent [19]

McGuirk

[11] Patent Number: 5,039,682

[45] Date of Patent: Aug. 13, 1991

[54] 6-FLUORO-1,4-DIHYDROQUINOL-4-ONE-3-CARBOXYLIC ACID DERIVATIVES AND INTERMEDIATES THEREFOR

[75] Inventor: Paul R. McGuirk, Ledyard, Conn.

[73] Assignee: Pfizer Inc., New York, N.Y.

[21] Appl. No.: 209,660

[22] Filed: Jun. 21, 1988

[51] Int. Cl.$^5$ .................. C07D 215/233; A61K 31/47
[52] U.S. Cl. .................. 514/312; 546/156; 556/110; 560/47; 564/431
[58] Field of Search ............ 546/156; 514/312

[56] References Cited

U.S. PATENT DOCUMENTS

| | | | |
|---|---|---|---|
| 3,472,859 | 10/1969 | Lesher | 260/287 |
| 3,753,993 | 8/1973 | Lesher et al. | 260/286 R |
| 3,907,808 | 9/1975 | Lesher et al. | 260/287 R |
| 3,960,868 | 6/1976 | Ferrini et al. | 546/156 |
| 4,146,625 | 3/1979 | Lee | 424/258 |
| 4,327,101 | 4/1982 | Mushika et al. | 424/258 |
| 4,556,658 | 12/1985 | Grohe et al. | 514/254 |
| 4,578,473 | 3/1986 | Domagala et al. | 546/156 |
| 4,623,650 | 11/1986 | Gilligan et al. | 514/312 |
| 4,636,506 | 1/1987 | Gilligan et al. | 514/256 |
| 4,665,079 | 5/1987 | Culbertson et al. | 514/312 |
| 4,670,444 | 6/1987 | Grohe et al. | 514/300 |
| 4,727,080 | 2/1988 | Soler | 514/312 |
| 4,762,844 | 8/1988 | Grohe et al. | 514/312 |
| 4,880,814 | 11/1989 | Chu et al. | 546/123 |
| 4,929,613 | 5/1990 | Culbertson et al. | 546/156 |
| 4,945,160 | 7/1990 | Kiely et al. | 546/156 |
| 4,956,465 | 9/1990 | Schriewer et al. | 546/156 |

FOREIGN PATENT DOCUMENTS

| | | |
|---|---|---|
| 28698 | 5/1981 | European Pat. Off. . |
| 230295 | 7/1987 | European Pat. Off. . |
| 235762 | 9/1987 | European Pat. Off. . |
| 236673 | 9/1987 | European Pat. Off. . |
| 255908 | 2/1988 | European Pat. Off. . |
| 270904 | 6/1988 | European Pat. Off. . |
| 2594439 | 6/1986 | France . |
| 1143339 | 7/1986 | Japan . |
| 1143364 | 7/1986 | Japan . |
| 1933 | 3/1989 | World Int. Prop. O. . |

OTHER PUBLICATIONS

Kang, J. et al., N-Cyclopropylation of Aromatic Amines, J. Chem. Soc., Chem. Commun. 1987, pp. 897–898.

Yamamoto, H. et al., Novel N-Alkylation of Amines with Organocopper Reagents, J. Org. Chem., 45: 2739–2740 (1980).

Iwao, M. et al., Directed Metalation of Tertiary Benzamides, Ortho N-Aryl Amination and Synthesis of Acridones, J. Am. Chem. Soc. 104: 5531–5533 (1982).

Abstract for JP 143339 (7/1/86).

Abstract for JP 143364 (7/1/86).

*Primary Examiner*—Mukund J. Shah
*Assistant Examiner*—E. Bernhardt
*Attorney, Agent, or Firm*—Peter C. Richardson; J. Trevor Lumb; Gregg C. Benson

[57] ABSTRACT

This invention relates to novel 1,7-disubstituted-6-fluoro-1,4-dihydroquinol-4-one-3-carboxylic acid derivatives and certain esters and cation salts thereof. This invention further relates to preparation of the compounds, antibacterial compositions containing the compounds and methods of using the compounds.

This invention also relates to a novel process for preparing novel N-cyclopropyl intermediates useful for preparing certain of the 1,7-disubstituted-6-fluoro-1,4-dihydroquinol-4-one-3-carboxylic acid derivatives of this invention which contain a cyclopropyl substituent at the 1 position as well as other 1,4-dihydroquinol-4-one-3-carboxylic acid derivatives so substituted with cyclopropyl.

8 Claims, No Drawings

6-FLUORO-1,4-DIHYDROQUINOL-4-ONE-3-CARBOXYLIC ACID DERIVATIVES AND INTERMEDIATES THEREFOR

BACKGROUND OF THE INVENTION

This invention relates to novel 1,7-disubstituted-6-fluoro-1,4-dihydroquinol-4-one-3-carboxylic acid derivatives and certain esters and cation salts thereof. This invention further relates to preparation of the compounds, antibacterial compositions containing the compounds and methods of using the compounds.

This invention also relates to a novel process for preparing novel N-cyclopropyl intermediates useful for preparing certain of the 1,7-disubstituted-6-fluoro-1,4-dihydroquinol-4-one-3-carboxylic acid derivatives of this invention which contain a cyclopropyl substituent at the 1 position as well as other 1,4-dihydroquinol-4-one-3-carboxylic acid derivatives so substituted with cyclopropyl.

While certain substituted 1,4-dihydroquinol-4-one-3-carboxylic acid derivatives are known and have been previously disclosed as antibacterial agents, there is a continuing need for novel antibacterial compounds for use in combating bacterial infections.

Therefore, it is an object of this invention to provide novel 1,7-disubstituted-6-fluoro-1,4-dihydroquinol-4-one-3-carboxylic acid derivatives and certain esters and cation salts thereof. Further, it is an object of this invention to provide novel 1,7-disubstituted-6-fluoro-1,4-dihydroquinol-4-one-3-carboxylic acid derivatives and certain esters and cation salts thereof which are useful as antibacterial agents. Still further, it is an object of this invention to provide methods for preparing the novel 1,7-disubstituted-6-fluoro-1,4-dihydroquinol-4-one-3-carboxylic acid derivatives and certain esters and cation salts thereof.

Another object of this invention is to provide a novel process for the preparation of novel N-cyclopropyl substituted compounds useful as intermediates in the preparation of 1,4-dihydroquinol-4-one-3-carboxylic acid derivatives containing a cyclopropyl substituent at the 1 position.

Yet another object of this invention is to provide antibacterial compositions comprising the novel compounds of this invention. Another object still of this invention is to provide methods of using the novel compounds of this invention in the treatment of a host suffering from bacterial disease.

SUMMARY OF THE INVENTION

This invention relates to certain novel substituted 1,4-dihydroquinol-4-one-3-carboxylic acid derivatives of the formula

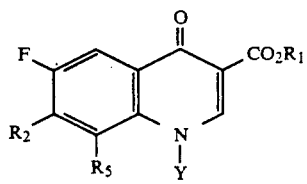

wherein
$R_5$ is H, F, Cl, $OCH_3$ or Z;
$R_1$ is H, ($C_1$–$C_7$)alkyl, benzyl or a pharmaceutically acceptable cation;

$R_2$ is vinyl, W substituted vinyl, $CH_3C\equiv C-$, $W-CH_2C\equiv C-$, cyclopropyl or

W is $R_3-(CH_2)_m-$; m is 1 or 2; $R_3$ is OH, $NH_2$, $NH(C_1-C_3)$alkyl, $SO_2(C_1-C_3)$alkyl, $SO_2NH(C_1-C_3)$alkyl or $SO_2NH_2$;
Y is $(C_1-C_3)$alkyl, $(C_1-C_3)$haloalkyl, cyclopropyl, vinyl, p-fluorophenyl or o,p-difluorophenyl; or $R_5$ is Z and Z is taken together with Y and have the formula

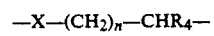

wherein X is $CH_2$ or O and is bonded to position 8 of the quinolone ring; n is 0, 1 or 2; and $R_4$ is selected from the group consisting of hydrogen, alkyl and haloalkyl of 1 to 3 carbons, hydroxymethyl, hydroxyethyl, aminomethyl, phenyl and methylene; and the pharmaceutically acceptable salts thereof.

Preferred compounds of the invention are those where $R_5$ is H or F, those where $R_2$ is cyclopropyl and those where Y and $R_2$ are each cyclopropyl.

Still more preferred compounds of the invention are those wherein $R_1$ is hydrogen or a pharmaceutically acceptable cation.

Specific preferred compounds of the invention are 1-ethyl-6-fluoro-7-vinyl-1,4-dihydroquinol-4-one-3-carboxylic acid, 1-ethyl-6-fluoro-7-cyclopropyl-1,4-dihydroquinol-4-one-3-carboxylic acid, 1-ethyl-6,8-difluoro-7-cyclopropyl-1,4-dihydroquinol-4-one-3-carboxylic acid, 1-ethyl-6,8-difluoro-7-vinyl-1,4-dihydroquinol-4-one-3-carboxylic acid, 1-cyclopropyl-6-fluoro-7-cyclopropyl-1,4-dihydroquinol-4-one-3-carboxylic acid and 1-ethyl-6,8-difluoro-7-(2-hydroxymethylcycloprop-1-yl)-1,4-dihydroquinol-4-one-3-carboxylic acid.

The present invention also relates to the novel process of preparing novel compounds of the formula

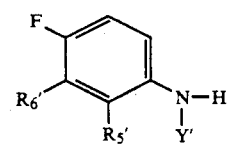

wherein $R_6'$ is F, Cl or Br, Y' is cyclopropyl and $R_5'$ is H, F, Cl, Br or $OCH_3$, which comprises contacting about 3–5 equivalents of cyclopropyl lithium in a reaction-inert solvent and oxygen free environment with about one equivalent of a compound of the formula

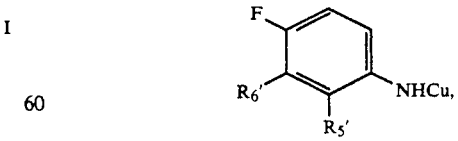

wherein $R_6'$ and $R_5'$ are as defined above, at a reaction temperature of from about $-80°$ C. to about $-40°$ C.; warming the reaction mixture from about $0°$ C. to about $35°$ C. and treating the reaction mixture at about $-78°$ C. with $O_2$. Certain of the compounds of formula VIII' wherein $R_6'$ is Br and $R_5'$ is H, F, Cl, Br or $OCH_3$ are useful in the preparation of compounds of formula I wherein Y' is cyclopropyl. Still other compounds of formula VIII' are useful in the preparation of other 1,4-dihydroquinol-4-one-3-carboxylic acid derivatives containing a cyclopropyl substituent at the 1 position.

Further, the present invention relates to the use of the novel compounds of formula VIII', above, to produce the novel compounds of the formula

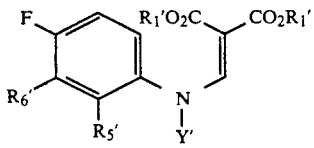

IX wherein $R_5'$, $R_6'$ and Y' are as defined above and $R_1'$ is $C_1-C_7$alkyl or benzyl.

Further, the present invention relates to antibacterial compositions comprising an antibacterially acceptable carrier and a compound of formula I. Preferred compositions contain the preferred compounds of formula I as described above.

Still further, the invention comprises a method of treating a host such as an animal or human being affected by a bacterial disease by administering to said host an antibacterially effective amount of a compound of formula I. Preferred methods of treatment administer a preferred compound of formula I as described above.

DETAILED DESCRIPTION OF THE INVENTION

According to the method described in U.S. Pat. No. 4,623,650, the compounds of formula I, where $R_2$ is as defined above except for cyclopropyl or

, are prepared by transition metal catalyst coupling of an appropriate organometallic compound containing group $R_2$ (except cyclopropyl or

 )

with the appropriate 7-$R_6$-quinolone ester of the formula II

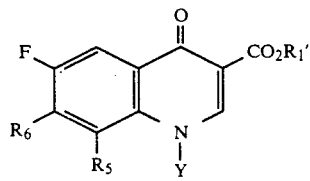

II wherein $R_5$ and Y are as defined above, $R_1'$ is $(C_1-C_7)$alkyl or benzyl and $R_6$ is bromo or iodo.

Where compounds of formula I having $R_2$ as cyclopropyl are desired, then the compound of formula III

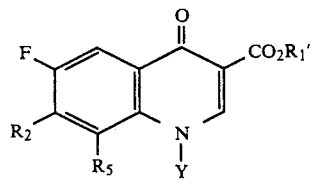

III where $R_2$ is vinyl and which is produced according to the above procedure is converted to a compound of formula III wherein $R_2$ is cyclopropyl by cyclizing the vinyl substituent according to conventional means in the presence of diazomethane or diiodomethane with zinc catalyst.

Further, when compounds of formula I above wherein $R_2$ is W substituted vinyl or W—$CH_2C\equiv C$— are desired, then such compounds are prepared by catalyst coupling of a tetrahydropyranyl (THP) protected propargyl alcohol metallic compound with the appropriate 7-$R_6$-quinolone ester of formula II, above. THP is then removed with p-toluenesulfonic acid in absolute ethanol by conventional methods where $R_2$ as propargyl is desired. Where cis-hydroxymethyl substituted vinyl is desired, hydrogenation is carried out with Lindlar's catalyst (palladium-on-calcium carbonate, lead poisoned) followed by removal of THP with p-toluenesulfonic acid in absolute ethanol by conventional methods.

Still further, when compounds of formula I above where $R_2$ is

are desired, then such compounds are prepared by catalyst coupling of an appropriate THP protected alkynylmetallic compound with the appropriate 7-$R_6$-quinolone ester of formula II above followed by hydrogenation with Lindlar's catalyst, cyclization in the presence of diazomethane and removal of THP with p-toluenesulfonic acid in absolute ethanol all according to conventional methods.

Such compounds wherein $R_3$ is OH may be further reacted with hydrazoic acid such as is described in Helvetica Chimica Acta, Vol. 59, Fasc. 6., pp. 2100-2113 (1976), and hydrogenated with Lindlar's catalyst to prepare compounds of formula I where $R_3$ is $NH_2$ or reacted with alkyl halides to give compounds of formula I where $R_3$ is $NH(C_1-C_3)$alkyl.

The coupling reaction is carried out in an inert solvent, particularly an ethereal solvent such as a dialkylether, e.g. diethylether or dipropylether, dimethoxyethane, or cyclic ethers such as tetrahydrofuran (THF). A hydrocarbon may be present with the ether, particularly an aromatic or aliphatic hydrocarbon containing from 5 to 10 carbon atoms, e.g. benzene or toluene.

The organometallic compound may be made by methods known in the art, some of which are as described below.

The organometallic compound may be prepared from the corresponding halide by direct lithium-halogen exchange using n-butyl, sec-butyl or t-butyl lithium followed by transmetallation by a wide variety of salts by known methods such as described by E. Negishi, Organometallics in Organic Synthesis, Vol. 1, page 104. The salts used are selected from salts of zinc, cadmium, magnesium, mercury, tin, silver, copper, and aluminum, preferably zinc. The most commonly used salts are the halides, particularly chlorides, bromides and iodides, and cyanides such as copper cyanide. The most advantageous salt is zinc chloride.

The above treatment with a butyllithium compound is best carried out in tetrahydrofuran at −78° to −50° C., preferably −78° C. Other suitable solvents besides THF are ethereal solvents alone or in admixture with an aliphatic or aromatic hydrocarbon solvent having from 5 to 10 carbon atoms such as benzene or toluene. Examples of suitable ethers are dialkylethers such as diethylether or dipropylether, dimethoxyethane and cyclic ethers.

Alternatively, the organometallic compounds may be formed by hydrogen-metal exchange between the corresponding alkene or alkyne compound and a strong base such as potassium t-butoxide-butyllithium or TMEDA-butyllithium.

The organometallic compound is coupled with the appropriate 7-$R_6$-quinolinone ester of formula II in the presence of 0.5–10 mole % of a transition metal catalyst at reaction temperatures generally ranging from room temperature to 50° C.

The transition metal catalysts are known, e.g. from Negishi, E., Acc. Chem. Res., 15, 340–348 (1982) and references cited therein. Suitable transition metals are platinum, cobalt, iron, zirconium, molybdenum, ruthenium, manganese, rhodium, preferably, nickel, palladium and platinum. These metals are combined with ligands such as $PPh_3$, $P(CH_3)_3$, and $P(C_2H_5)_3$, wherein Ph is phenyl. Preferred transition metal catalysts are $(PPh_3)_4Pd$, $(PPh_3)_2PdCl_2$, $(PPh_3)_4Ni$ and $(PPh_3)_2NiCl_2$. For the preparation of those compounds wherein Z and Y are taken together to form a tricyclic compound, $(PPh_3)_2NiCl_2$ is preferred.

Certain methods for preparation of the compounds of formula II are analogous to those described in the art.

The overall reactions of two prior art methods are set out in reaction path (III)→(IV)→(VI)→(VII)→(II) of Scheme A and in Scheme B below. That part of Scheme A wherein the reaction path is (IV)→(VIII)→(IX)→(II) and Y is cyclopropyl is novel. Further, certain compounds of formula (VIII) and (IX) are novel.

In Scheme A an aniline of formula IV wherein $R_5$ and $R_6$ are as defined above is reacted with a dialkyl or dibenzyl alkoxymethylene malonate of formula V wherein R' is an alkyl group of 1 to 7 carbon atoms and $R_1'$ is an alkyl group of 1 to 7 carbon atoms or benzyl. The reaction is generally carried out without solvent at about 100° to 200° C., preferably 150° to 175° C., for about 0.5 to 24 hours, usually for 0.5 to 2 hours. The resulting intermediates of formula VI are crystallized from a hydrocarbon or ethereal solvent such as light petroleum or diethyl ether and cyclized by heating at about 150° to 250° C. in high boiling solvents such as dichlorobenzene, tetralin, diphenyl ether or diethyleneglycol dimethylether, preferably Dowtherm A (Fluka Chemical Corp., Hauppauge, N.Y.) which is a commercially available high boiling point solvent mixture of diphenylether and dibenzofuran. The reaction time ranges from about 0.5 to 12 hours.

The intermediates of formula VII formed are N-substituted with a halide Y-Hal wherein Y is as defined above except cyclopropyl and Hal is halogen. Examples of suitable halides are ethyliodide, 2-fluoro-1-iodoethane, allylbromide and 2-bromoethanol. The adduct formed on reaction with 2-bromoethanol may be converted to a compound of formula I wherein Y is vinyl by hydroxyl activation with, for example, thionyl chloride followed by elimination with a suitable base such as triethylamine, diazabicycloundecene and diazabicyclononane. Generally, the substitution is carried out in DMF with an inorganic base such as potassium carbonate at temperatures ranging from room temperature to 110° C.

Scheme A

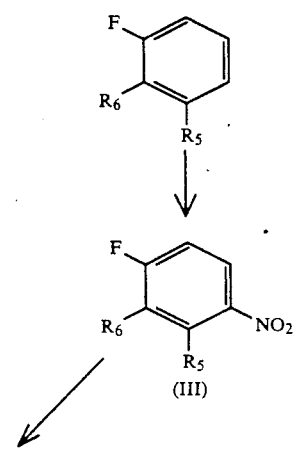

Scheme A

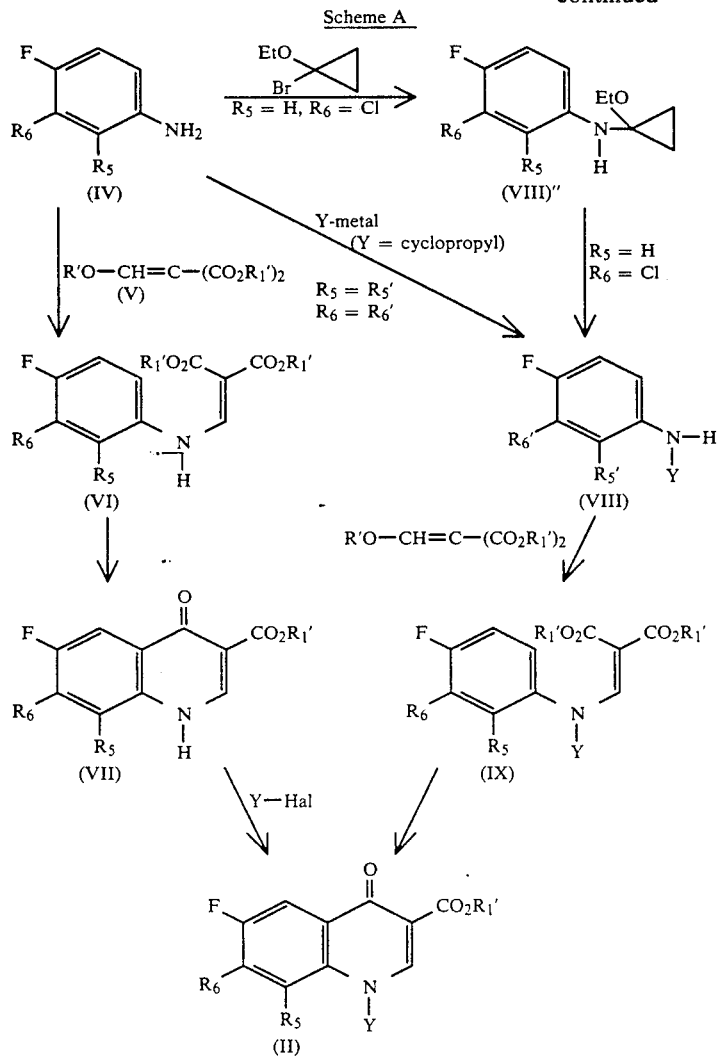

Scheme A'

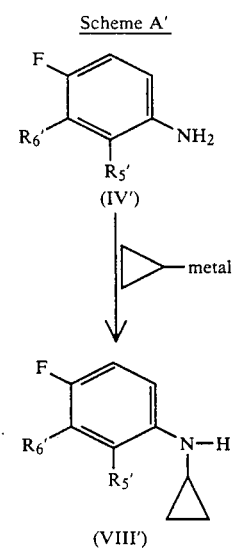

When compounds of formula II where Y is cyclopropyl are desired, the compounds of formula IV are reacted with about 3-5 mole equivalents of a cyclopropylmetallic compound prepared as described above for alkenyl and alkynyl metallic compounds in the presence of about 1.5 mole equivalent of cuprous cyanide and about one mole equivalent of a compound of formula IV in a reaction-inert solvent at a temperature of from about −80° C. to about −40° C. in the absence of oxygen. The reaction is generally run for about 15 to 24 hours. The reaction mixture is warmed to from about 0° C. to about 35° C., then cooled to −78° C. and oxygenated before recovery of the product of formula VIII. Following the same reaction, other novel compounds useful as intermediates are prepared as shown in Scheme A' wherein $R_5'$ and $R_6'$ are defined as above.

Alternatively, at least certain compounds of formula VIII can be prepared by 1-ethoxycyclopropylation of compounds of formula IV according to methods described by Kang, J. et al., J. Chem. Soc., Chem. Commun., 897-898, 1987. Such method, which is reported to give high yields and would therefore be a preferred route of synthesis for such compounds, comprises stirring an excess of 1-bromo-1-ethoxycyclopropane with compounds of formula IV in the presence of triethylamine in a non-polar refluxing solvent such as dichloromethane or pentane and reducing the resulting product in the presence of a Lewis acid. A particularly effective reducing agent for this method is a mixture of $NaBH_4$ (2 equivalents) and BF₃OEt₂ (2 equivalents) in tetrahydrofuran which has been stirred at 0° C. for 0.5 hour.

Compounds of formula IX are then prepared by reacting compounds of formula VIII with a dialkyl or dibenzyl alkoxymethylene malonate of formula V wherein R' is an alkyl group of 1 to 7 carbon atoms and R₁' is an alkyl group of 1 to 7 carbon atoms or benzyl under reaction conditions as described above for the conversion of compounds of formula IV to compounds of formula VI in Scheme A.

The mono- or di-fluoro anilines of formula IV, also used in the reaction of Scheme B hereinafter, may be prepared by conventional nitration and reduction methods such as disclosed by March, J., Adv. Org. Chem., Second Ed., McGraw Hill, 474, 1125 (1977) from the corresponding fluorobenzenes which are commercially available.

In Scheme B, a compound of formula VIII wherein R₆ and R₅ are as defined above except that R₅ is not Z is reacted with a dialkyl or dibenzyl alkoxymethylene malonate of formula V wherein R' is alkyl having from 1 to 7 carbon atoms and R₁' is an alkyl group of 1 to 7 carbon atoms or benzyl. The reaction conditions are as described above with reference to the conversion of compounds IV to VI in Scheme A.

The cyclization of compound IX formed above is effected by heating in an acidic medium such as polyphosphoric acid at about 100° to 250° C. for about 0.5 to 24 hours, preferably at 100° to 150° C. for 0.5 to 2 hours. This procedure is described by Albrecht, R., Prog. Drug Res., Vol. 21, 35–49 (1977). The resulting ester of formula II is usually purified by recrystallization or chromatography.

The compounds of formula VIII may be prepared from those of formula IV by conventional methods. For instance, in Scheme B, a compound of formula IV may be reacted with acetic anhydride in ethanol at about 25° to 100° C. The formed compound of formula X is reacted with a suitable base such as sodium hydride and N-substituted with an appropriate halide, tosylate or mesylate containing group Y.

Scheme B

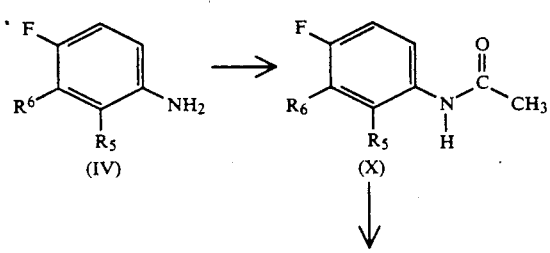

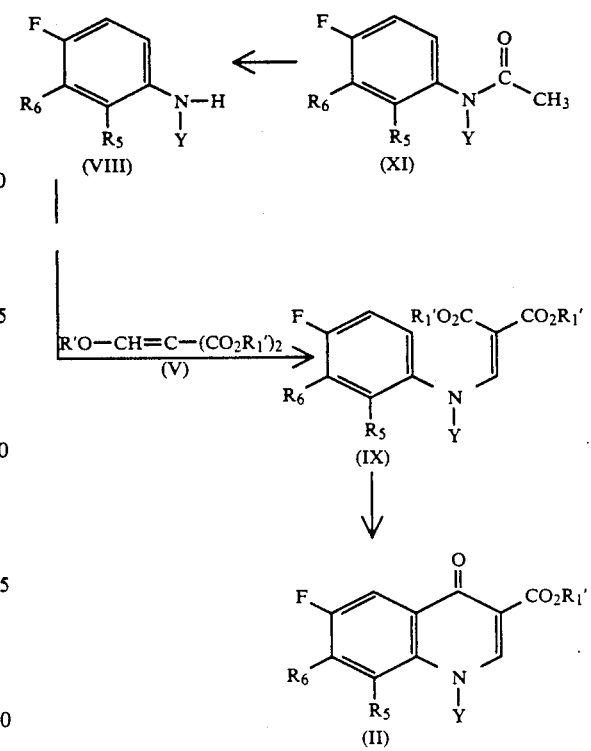

The acetal group in the formed compound of formula XI is removed by refluxing in aqueous medium such as 6N hydrochloric acid to form the compound of formula VIII.

Alternatively, N-substituted anilines of formula VIII may be formed by reductive amination with an appropriate aldehyde and a suitable reducing agent such as diborane, palladium on carbon with hydrogen, sodium borohydride or sodium cyanoborohydride as, for instance, is described in the above March reference at pages 819–820. Yet another method of forming N-substituted compounds of formula VIII is to react compounds of formula IV with an appropriate anhydride or acid chloride and direct reduction to compounds of formula VIII with diborane in THF.

The initial N-substitution of formula IV in Scheme B rather than those of Scheme A is particularly useful when Y is polyfluoroalkyl since substitution with polyfluoroalkyl halides is not a viable route.

The intermediates of formula II wherein R₅ and Y are taken together to form tricyclic compounds are prepared by the methods of Schemes C to H hereafter.

The initial compound used in these methods is 2,4-difluoro-3-bromo-1-nitrobenzene formed from 1,3-difluoro-2-bromobenzene by conventional nitration such as described in the above March reference, pages 474–476.

Scheme C shows the preparation of tricyclic intermediates of formula XVII having a five-membered third ring in which R₄ is as defined above.

Scheme C

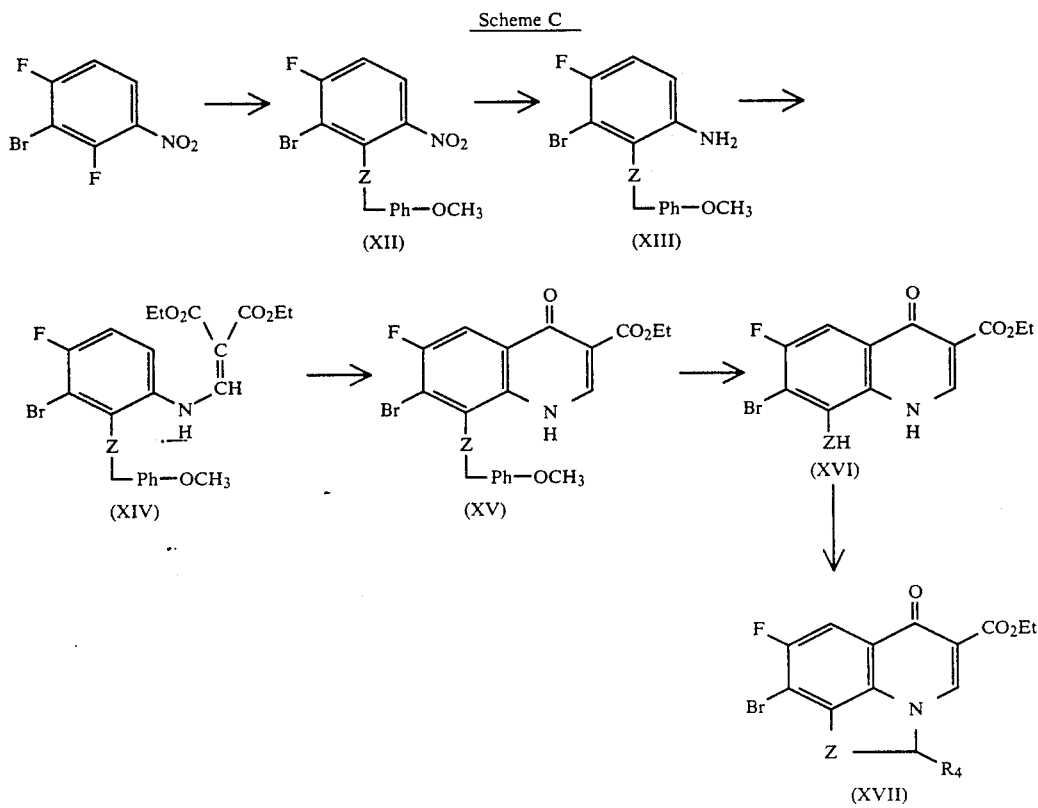

2-4-Difluoro-3-bromonitrobenzene is reacted with a reagent of the formula

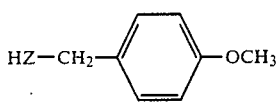

wherein Z is sulfur, oxygen, NH or NCH$_3$, in a polar organic solvent such as THF. When Z is sulfur, the reaction requires the presence of an organic base such as triethylamine. When Z is oxygen, a base such as sodium hydride is required for the reaction. Triethylamine, pyridine or another base is required when Z is NH or NCH$_3$ when only one equivalent of the above reagent is used.

The compound of formula XII is selectively reduced to the corresponding aniline by catalytic hydrogenation or by chemical reduction such as with stannous chloride in ethanol. After condensation of XIII with diethylethoxymethylene malonate at about 150° C., the compound of formula XIV is formed. Ring cyclization of XIV is by heating with e.g. Dowtherm A as the solvent. The substituted benzyl group is removed under acidic conditions e.g. with trifluoromethanesulfonic acid, trifluoroacetic acid and anisole.

The third ring is formed by reaction of XVI with R$_4$CHI$_2$ or R$_4$CHO wherein R$_4$ is as defined above to provide the compound of formula XVII.

Scheme D shows the preparation of tricyclic intermediates of formula XXIII wherein n is 0, 1 or 2, Z is S, NH or NCH$_3$ and R$_4$ is as defined above.

Scheme D

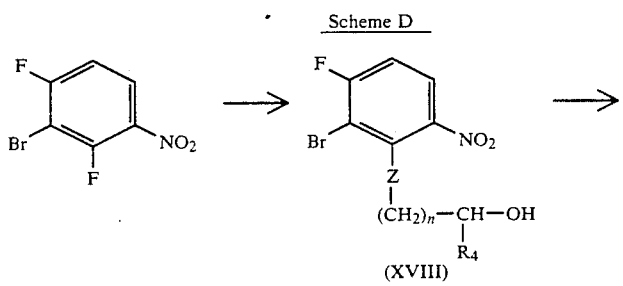

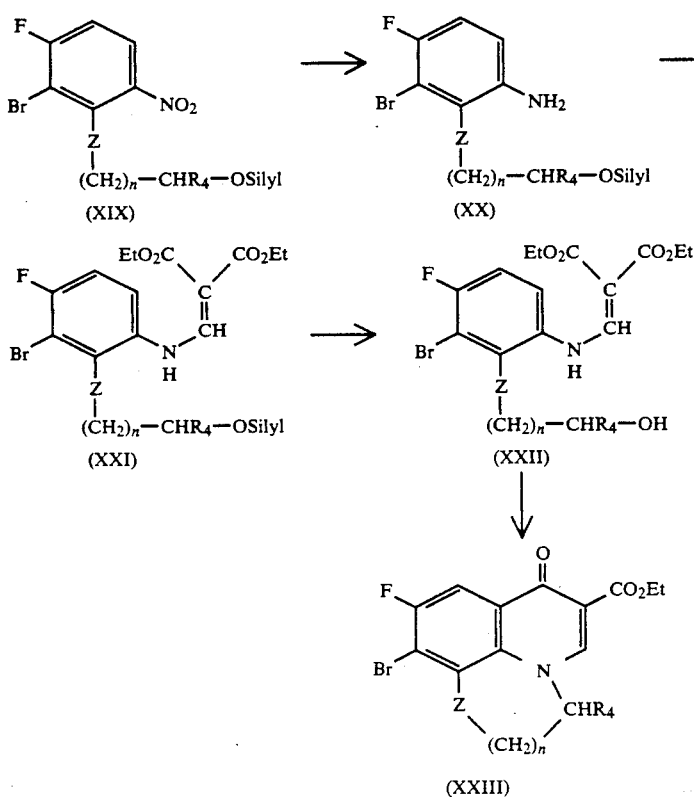

2,4-Difluoro-3-bromonitrobenzene is reacted with a compound of the formula HZ—(CH$_2$)$_n$—CHR$_4$—OH wherein Z is S, NH or NCH and n is 1 or 2, in a polar solvent such as THF at 0° C. to room temperature. When Z is S, a base is needed such as triethylamine. The compound of formula XVIII is reacted with a compound providing a protecting group such as a silyl group, specifically t-butyldimethylsilyl chloride, usually in DMF and imidazole, to form the compound of formula XIX. The next sequence of steps is the same as described with reference to Scheme B. Thus, there is hydrogenation of the nitro group and condensation with diethylethoxymethylene malonate. The compound of formula XXI is treated with fluoride to remove the protecting silyl group and cyclization is attained, after first reacting XXII with triphenylphosphine and ethylazodicarboxylate to close the second ring, by heating with polyphosphoric acid or ester at about 120° to 150° C. for 0.5 to 2 hours. "Silyl" is a trialkyl silyl group of the formula

wherein R″ is independently an alkyl group of 1–4 carbon atoms.

In Scheme E is illustrated the preparation of tricyclic intermediates of formula XXIX wherein n and R$_4$ are as defined above.

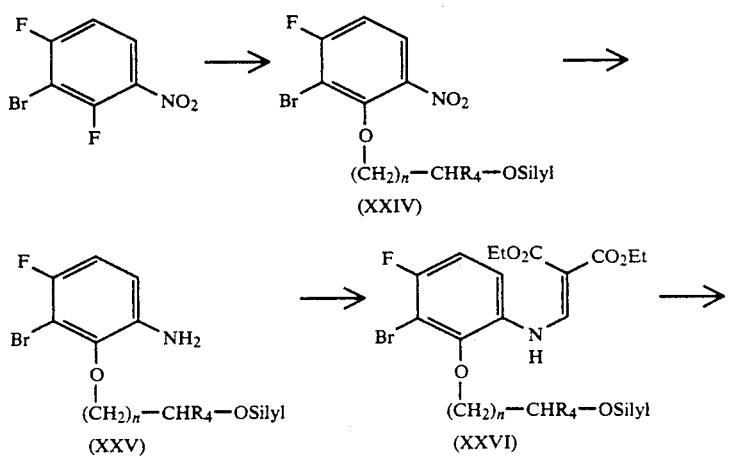

Scheme E

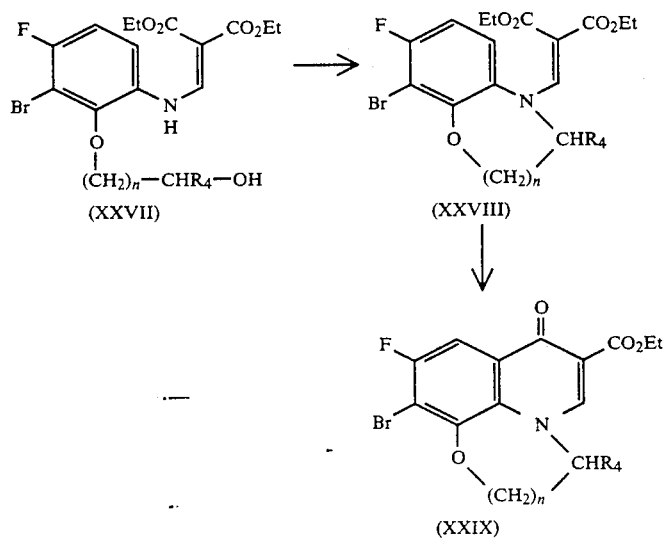

2,4-Difluoro-3-bromonitrobenzene is reacted with a monoprotected diol of formula Silyl—O—$(CH_2)_n$—$CHR_6$—OH and a base like sodium hydride in THF at 0° C. to room temperature to give a compound of formula XXIV. In a sequence identical to that of Scheme D, intermediate XXIV is converted to XXIX by reduction of the nitro group, condensation with ethoxymethylene malonate to give XXVI, deprotection with fluoride, cyclization of the second ring with triphenylphosphine and ethyl azodicarboxylate and cyclization to the tricyclic compound with polyphosphate acid or ester at 120° C. to 150° C. for 0.5 to 2 hours.

Scheme F illustrates other methods for synthesis of tricycles of formula XXIX. 2,4-Difluoro-3-bromonitrobenzene is reacted either directly with a hydroxyketone HO$(CH_2)_n$C(O)$R_4$ wherein $R_4$ and n are as defined above or first with potassium hydroxide in DMSO to give phenol XXX and then with an haloketone X$(CH_2)_n$C(O)$R_4$ with $R_4$ as defined above, n as 1 or 2 and X halogen to give common intermediate XXXI. The compound XXXI undergoes reductive cyclization to give benzoxazine XXXII. The compound XXXII is then condensed with ethoxymethylene malonate and cyclized in polyphosphate acid or ester using conditions described above to provide tricycle XXIX.

Scheme F

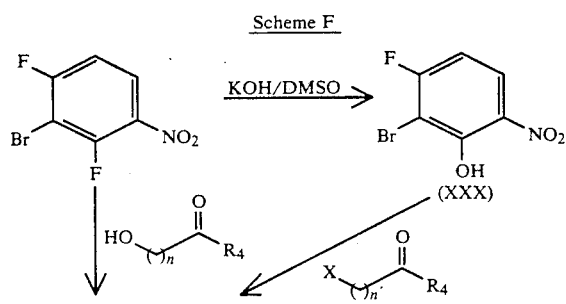

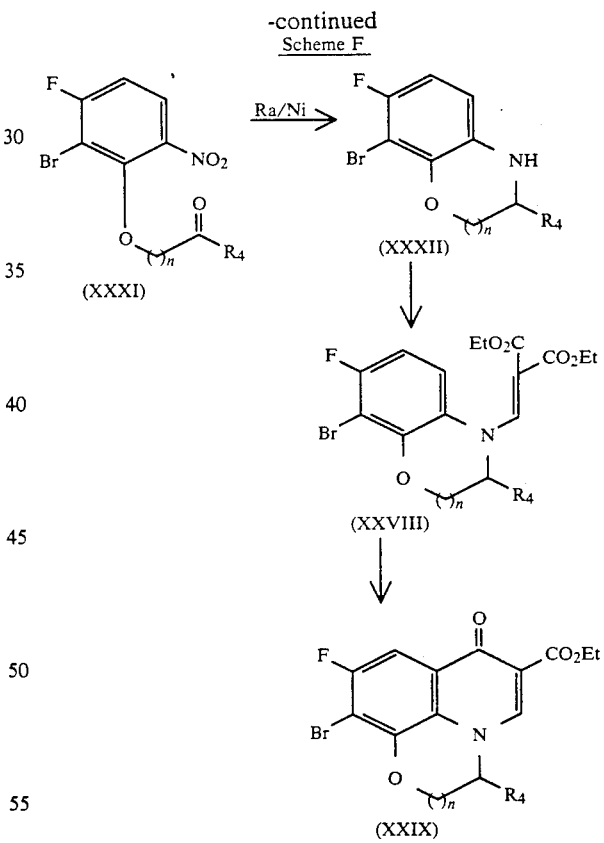

Schemes G and H illustrate the synthesis of tricyclic intermediates wherein Z is $CH_2$ and $R_4$ and n are as defined above.

Scheme G illustrates the synthesis of tricyclic intermediates of formula XLI having a five-membered third ring. 2,4-Difluoro-3-bromonitrobenzene is reacted with diethylsodiomalonate in THF at 0° C. to room temperature to give intermediate XXXIII. Monodecarboxylation is effected with para-toluene sulfonic acid in THF and water at 80° C. The resulting ester XXXIV is reduced with diborane in THF at 50° C. for 48 hours.

Protection of the alcohol with a "silyl" protecting group and reduction of the nitro group with Raney-Nickel in ethanol gives intermediate aniline XXXVII. Through the identical sequence of steps described in Schemes D, E and F, the tricyclic compound XLI is formed.

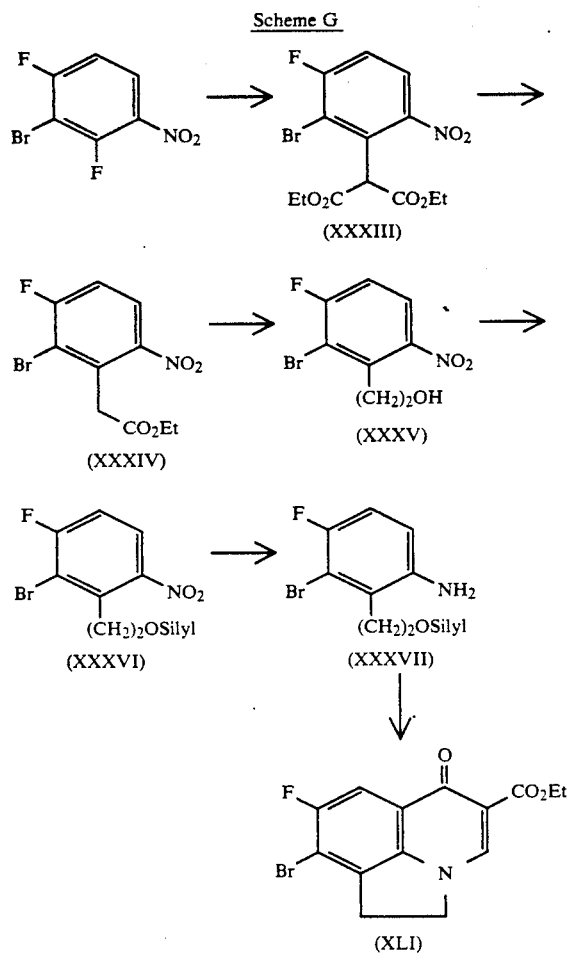

In Scheme H is illustrated the preparation of tricyclic intermediates of formula XLIX having six and seven-membered third rings wherein $R_4$ is as defined above and n is 1 or 2. Using intermediate XXXVII from Scheme G, the silyl group is removed and the hydroxyl group in resulting compound XXXVII is activated by reaction with para-toluene sulfonyl chloride in $CH_2Cl_2$ and pyridine. Addition of either one or two carbon atoms is accomplished by reaction of XLII (wherein Ts is p-toluenesulfonyl) with KCN, the anion of dithioacetal

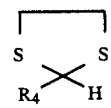

or the anion of $R_4$-functionalized diethyl malonate

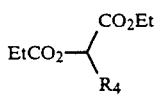

wherein $R_4$ is as defined above. The resulting intermediates of carbanion addition are subjected to hydrolysis, decarboxylation if necessary, and reduction by standard methods to give intermediate XLIII wherein n is 1 or 2. "Silyl" protection, reduction of the nitro group to give aniline XLV and diethyl ethoxymethylene malonate condensation gives XLVI. The protecting group is removed by treatment with fluoride ion and the second and third rings are formed by triphenyl phosphine, ethyl azodicarboxylate and polyphosphoric acid or ester, respectively, to give intermediate XLIX wherein n is 1 or 2.

Compounds (I) wherein $R_1$ is hydrogen are obtained by acid or base hydrolysis of the corresponding esters wherein $R_1$ is alkyl or benzyl, or by hydrogenolysis of corresponding compounds wherein $R_1$ is benzyl.

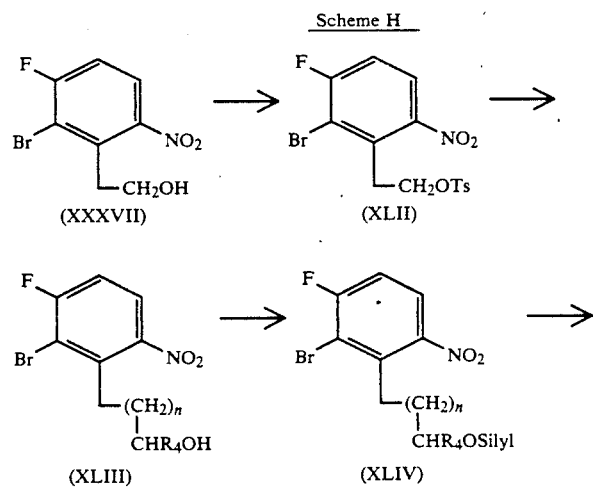

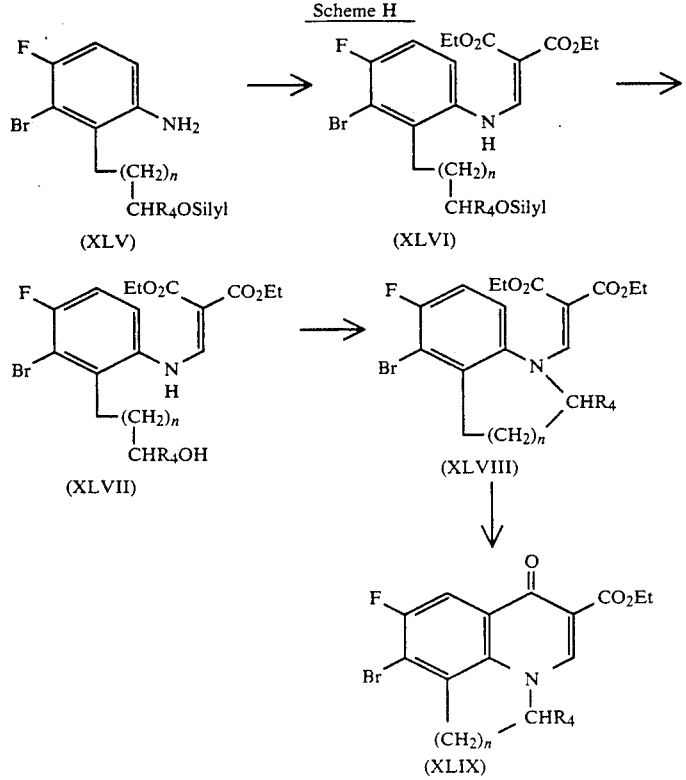

Scheme H

The pharmaceutically acceptable cation salts of the compounds of formula I may be prepared by conventional methods. For instance, the salts may be prepared by treating the compound of formula I in which $R_1$ is hydrogen with an aqueous solution of the desired pharmaceutically acceptable cation and evaporating the resulting solution to dryness, preferably under reduced pressure. Suitable pharmaceutically acceptable cations for this purpose include alkali metal salts such as potassium, sodium, and lithium salts, alkaline earth metal salts such as calcium and magnesium salts, ammonium salts and organic amine salts such as choline and diethanolamine salts.

The invention includes the acid addition salts of the compounds of formula I wherein $R_1$ is hydrogen and group $R_2$ has a nitrogen basic enough to be protonated with an acid. Particularly, pharmaceutically acceptable acid addition salts are included such as hydrochloric acid salts. These salts may be prepared in a conventional manner, e.g. by treating a solution or suspension of a compound of formula I with one chemical equivalent of an acid. Conventional concentration or crystallization techniques are employed in isolating the salts. Illustrative of suitable salts are those of acetic, lactic, succinic, maleic, tartaric, citric, gluconic, ascorbic, benzoic, cinnamic, fumaric, sulfuric, phosphoric, hydrochloric, sulfamic and sulfonic, such as methanesulfonic, benzenesulfonic and p-toluenesulfonic acids.

The sodium and potassium cation salts are preferred for parenteral administration because of their water solubility.

The compounds of the invention can be administered alone, but will generally be administered in admixture with a pharmaceutically acceptable carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5-1000 ppm, preferably 10-300 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.25-25 mg/kg/day, advantageously 0.5-10 mg/kg/day given in a single daily dose or up to 3 divided doses.

The invention also provides pharmaceutical compositions comprising an antibacterially effective amount of a compound of the formula I together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5-50 mg/kg/day given in a single dose or up to 3 divided doses. For intramuscular or intravenous administration, dosage levels are about 0.1-200 mg/kg/day, advantageously 0.5-50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The invention yet further provides a method of treating an animal, including a human being, having a bacterial disease which comprises administering to the animal an antibacterially effective amount of a compound of the formula I or a pharmaceutical composition as defined above.

The antibacterial activity of the compounds of the invention is shown by testing according to the Steer's replicator technique which is a standard in vitro bacterial testing method described by E. Steers et al., *Antibiotics and Chemotherapy,* 9, 307 (1959).

The following examples serve to illustrate the invention and are not to be construed as limiting in any way the scope of the invention to the examples shown.

EXAMPLE 1

Ethyl 1-ethyl-6-fluoro-7-vinyl-1,4-dihydroquinol-4-one 3-carboxylate

Into a 250 ml flask which had been flame dried and nitrogen purged was placed 8.8 ml (8.77 mmoles) of 1N vinyl magnesium bromide which was then cooled to −78° C. under nitrogen causing a precipitate to form. Then, a solution containing 1.59 g (11.7 mmoles) of anhydrous fused zinc chloride in 20 ml of anhydrous tetrahydrofuran was added. The resulting suspension was warmed to −20° C. and, sequentially, 1.00 g (2.92 mmoles) of ethyl 1-ethyl-6-fluoro-7-bromo-1,4-dihydroquinol-4-one 3-carboxylate (Preparation E) in 20 ml of anhydrous tetrahydrofuran followed by 0.34 g (10 mole %) of tetrakis(triphenylphosphine)palladium were added. The reaction was warmed to room temperature and maintained at room temperature for 1.3 hours. The reaction suspension was added to a separatory funnel containing equal volumes of ethyl acetate and saturated ammonium chloride and extracted, the organic layer washed twice with saturated ammonium chloride, the combined ammonium chloride layers washed once with ethyl acetate and the wash combined with the product solution. The combined product solution was washed once with saturated brine, dried over anhydrous sodium sulfate, filtered, concentrated in vacuo and column chromatographed on silica gel (95% ethyl acetate/hexanes, 1% triethylamine). Recrystallization from hot benzene gave a 50% yield (0.416 g) of the title compound as light orange crystals, m.p. 155°–160° C.
Elemental Analysis:
Calculated: C, 66.44; H, 5.54; N, 4.84%.
Found: C, 66.46; H, 5.55; N, 4.73%.

EXAMPLE 2

1-Ethyl-6-fluoro-7-vinyl-1,4-dihydroquinol-4-one 3-carboxylic acid

To 0.308 g (1.07 mmoles) of ethyl 1-ethyl-6-fluoro-7-vinyl-1,4-dihydroquinol-4-one 3-carboxylate (Example 1) was added 8 ml of tetrahydrofuran and 8 ml of 1N hydrochloric acid. The mixture was refluxed for 24 hours. The tetrahydrofuran was evaporated by removing the reflux condenser. The remaining contents, including a precipitate, were diluted with deionized water, chilled in wet ice, suction filtered and washed several times with deionized water and then diethyl ether. The precipitate was then air-dried for one hour which gave a yield of 92.8% (0.258 g) of the title compound as granular, light tan crystals, partial m.p. ∼220° C.

EXAMPLE 3

Ethyl 1-ethyl-6-fluoro-7-cyclopropyl-1,4-dihydroquinol-4-one 3-carboxylate

To a first mixture of 15 ml of 40% potassium hydroxide and 15 ml of 1:1 ether/ethyl acetate at 0° C. was added 1.27 g (8.65 mmoles) of N-methyl-N'-nitro-N-nitrosoguanidine. A second mixture was prepared with 0.250 g (0.865 mmoles) of ethyl 1-ethyl-6-fluoro-7-vinyl-1,4-dihydroquinol-4-one 3-carboxylate (Example 1), 50 ml of 7:1:1 ethyl acetate/diethyl ether/chloroform and 0.001–0.002 equivalents of palladium (II) acetate. The second mixture was also cooled to 0° C. The first mixture was added quickly to the second mixture resulting in an immediate reaction with rapid evolution of gas. The reaction mixture was extracted with ethyl acetate/deionized water and the organic layer washed once with 1:1 acetic acid/deionized water, then washed several times with a saturated sodium bicarbonate solution and then twice with saturated brine. The organic layer was dried over anhydrous sodium sulfate, suction filtered, concentrated in vacuo and column chromatographed on silica gel (90% ethyl acetate, 9% hexane, 1% triethylamine). The solvent residue was removed by high vacuum which gave 0.174 g of a pink solid containing an impurity.

Therefore, the above procedure was repeated with the exception that the reaction with diazomethane and palladium (II) acetate was repeated three times which, following recrystallization from alcohol, gave a yield of 33.2% (0.122 g) of the title compound as a faint pink solid, m.p. 160°–161° C.

EXAMPLE 4

1-Ethyl-6-fluoro-7-cyclopropyl-1,4-dihydroquinol-4-one 3-carboxylic acid

To 4 ml of 1N hydrochloric acid and 4 ml of tetrahydrofuran was added 0.110 g (0.363 mmoles) of ethyl 1-ethyl-6-fluoro-7-cyclopropyl-1,4-dihydroquinol-4-one 3-carboxylate (Example 3). The mixture was refluxed for 17 hours. Then, the tetrahydrofuran was evaporated by removing the reflux condenser. The resulting precipitate was suction filtered, washed with deionized water, washed with ether and then dried for 3 hours which gave a yield of 86% (0.086 g) of the title compound as shiny, white crystals, m.p. 221°–223° C.

EXAMPLE 5

1-Ethyl-6,8-difluoro-7-cyclopropyl-1,4-dihydroquinol-4-one 3-carboxylic acid

A. Ethyl 1-ethyl-6,8-difluoro-7-vinyl-1,4-dihydroquinol-4-one 3-carboxylate

To 25 ml of vinyl magnesium bromide (25 mmoles, 1N tetrahydrofuran) was added 4.5 g of anhydrous zinc chloride in 50 ml of dry tetrahydrofuran at room temperature. Then, 3.0 g (8.3 mmoles) of ethyl 1-ethyl-6,8-difluoro-7-bromo-1,4-dihydroquinol-4-one 3-carboxylate (Preparation A) as a solid and 3.0 g of tetrakis (triphenylphosphine)palladium were added. The reaction mixture was heated to 40° C for 18 hours, cooled to room temperature and then poured into saturated aqueous ammonium chloride and ethyl acetate. The aqueous layer was extracted twice with 150 ml of ethyl acetate, then the organic phase was dried over sodium sulfate, filtered and concentrated in vacuo. The crude concentrate was chromatographed on silica gel with 60% ethyl acetate/hexane and gave a yield of 16% (400 mg) of ethyl 1-ethyl-6,8-difluoro-7-vinyl-1,4-dihydroquinol-4-one 3-carboxylate as a white solid, m.p. 130°-133° C.

B. Ethyl 1-ethyl-6,8-difluoro-7-cyclopropyl-1,4-dihydroquinol-4-one 3-carboxylate To 100 mg (0.33 mmoles) of ethyl 1-ethyl-6,8-difluoro-7-vinyl-1,4-dihydroquinol-4-one 3-carboxylate (Part A, above) in 70 ml of ethyl acetate at 5° C. was added excess diazomethane in diethyl ether and catalytic palladium (II) acetate. The reaction was stirred for 30 minutes at 5° C. The excess diazomethane was quenched with acetic acid. Then, the reaction mixture was poured into deionized water and extracted with saturated aqueous sodium bicarbonate. The organic phase was then dried over sodium sulfate, filtered and concentrated in vacuo. The crude concentrate was chromatographed to give a yield of 87% (92 mg) of 1-ethyl-6,8-difluoro-7-cyclopropyl-1,4-dihydroquinol-4-one 3-carboxylic acid ethyl ester as a white solid, m.p. 128-130° C. Alternatively, to 260 mg (0.85 mmoles) of ethyl 1-ethyl-6,8-difluoro-7-vinyl-1,4-dihydroquinol-4-one 3-carboxylate (Part A, above) in 100 ml of ethyl acetate was added 90% excess diazomethane in diethyl ether and catalytic palladium (II) acetate. The reaction mixture was stirred for 2 hours at 5° C. and then the diazomethane was quenched with acetic acid. The quenched reaction mixture was poured into deionized water and extracted with saturated aqueous sodium bicarbonate. The organic phase was dried over sodium sulfate, filtered and concentrated in vacuo. The crude concentrate was chromatographed on silica gel (100% ethyl acetate) to give a yield of 90% (246 mg) of ethyl 1-ethyl-6,8-difluoro-7-cyclopropyl-1,4-dihydroquinol-4-one 3-carboxylate as a white solid, m.p. 128°-130° C.

C. 1-Ethyl-6,8-difluoro-7-cyclopropyl-1,4-dihydroquinol-4-one 3-carboxylic acid 134 mg (0.42 mmoles) of ethyl 1-ethyl-6,8-difluoro-7-cyclopropyl-1,4-dihydroquinol-4-one 3-carboxylate (Part B, above) was hydrolyzed in 1N hydrochloric acid/tetrahydrofuran/acetic acid at 120° C. for 2 hours. Then, the reaction mixture was cooled to room temperature and the resulting precipitate was collected by suction filtration and air-dried. The precipitate was recrystallized from DMSO to give a yield of 89% (110 mg) of the title compound as a white solid, m.p. 238°-239° C.

EXAMPLE 6

Ethyl 1-ethyl-6,8-difluoro-7-(3-hydroxy-1-propynyl)-1,4-dihydroquinol-4-one-3-carboxylate A. A first solution containing 13.6 g (97.2 mmoles) of tetrahydropyranyl (THP) protected propargyl alcohol (propinol) in 500 ml of tetrahydrofuran was cooled to −78° C. and 40 ml (97.2 mmoles) of 2.5M n-butyl lithium was added slowly dropwise. Separately, 20.0 g (117 mmoles) of anhydrous zinc chloride was placed in a flask under high vacuum and fused with heat from a propane torch. The flask was allowed to cool to room temperature and 200 ml of tetrahydrofuran was added to dissolve the zinc chloride with heating and stirring. The dissolved zinc chloride was added by cannula to the first solution at −78° C. and then the mixture was warmed to −40° C. To the mixture were added 3.0 g (2.59 mmoles) of tetrakis(triphenylphosphine)palladium and 10 g (27.7 mmoles) of ethyl 1-ethyl-6,8-difluoro-7-bromo-1,4-dihydroquinol-4-one 3-carboxylate (Preparation A) as solids. The reaction mixture was warmed slowly to room temperature, then to 50° C. for 36 hours. Then, the reaction was cooled to room temperature and poured into 500 ml of saturated aqueous ammonium chloride and extracted twice with 500 ml of ethyl acetate. The organic phase was dried over sodium sulfate, filtered and concentrated in vacuo. The resulting crude oil was chromatographed on silica gel (70% ethyl acetate/hexanes) to give a yield of 43% (4.94 g) of ethyl 1-ethyl-6,8-difluoro-7-(3-tetrahydropyranyl)oxy-1-propynyl)-1,4-dihydroquinol-4-one 3-carboxylate as a yellow solid after trituration with 50:50 ether/hexanes, m.p. 137°-138° C.

B. To 20 ml of absolute ethanol was added 0.5 g (1.19 mmoles) of ethyl 1-ethyl-6,8-difluoro-7-(3-(tetrahydropyranyl)oxy-1-propynyl)-1,4-dihydroquinol-4-one 3-carboxylate (Part A, above) and 0.011 g (0.0597 mmoles) of p-toluene sulfonic acid monohydrate. The reaction mixture was then refluxed for 2.0 hours. The reaction mixture was cooled to 0° C. and maintained at 0° C. for 1 hour. The resulting precipitate was suction filtered, washed with cold ethanol and air-dried to give a yield of 85.2% (0.340 g) of the title compound of this Example as a light beige solid, m.p. 206°-208° C.

EXAMPLE 7

1-Ethyl-6,8-difluoro-7-(3-hydroxy-1-propynyl)-1,4-dihydroquinol-4-one 3-carboxylic acid To a mixture of 7.0 ml of 1N hydrochloric acid and 7.0 ml of tetrahydrofuran was added 0.280 g (0.836 mmoles) of ethyl 1-ethyl-6,8-difluoro-7-propinol-1,4-dihydroquinol-4-one 3 carboxylate (Example 6). The reaction mixture was refluxed for 11 hours and then cooled to room temperature. The resulting precipitate was suction filtered, washed with deionized water and ether and dried in a drying pistol. The resulting product was suspended in 20 ml of methanol, suction filtered to remove impurities and air-dried to give a yield of 75.1% (0.193 g) of the title compound, m.p. 258°-260° C.

EXAMPLE 8

Ethyl 1-ethyl-6,8-difluoro-7-(3-tetrahydropyranyl)-oxy-1-propenyl)-1,4-dihydroquinol-4-one 3-carboxylate A. To 50 ml of ethyl acetate in a Parr hydrogenation bottle was added 0.283 g (0.675 mmoles) of ethyl 1-ethyl-6,8-difluoro-7-(3-(tetrahydropyranyl)oxy-1-propynyl)-1,4-dihydroquinol-4-one 3-carboxylate (Example 6, Part A) and 0.10 g Lindlar's catalyst (palladium-on-calcium carbonate; lead poisoned). The mixture was hydrogenated at 15 psi of hydrogen for about 3 hours which showed incomplete conversion. Then, another 53 mg of Lindlar's catalyst was added to the reaction mixture and the mixture was hydrogenated further at 20 psi of hydrogen overnight. The mixture was suction filtered through a Celite ® (Johns-Mansville Corp.) pad using hot ethyl acetate and the filtrate was completely stripped of solvent in vacuo. The resulting solid was dissolved in approximately 3 ml of benzene, ml of hexanes was then added to the solution and the solution chilled in a refrigerator. The resulting crystallized solid was recovered by suction filtration, washed with hexanes and air-dried to give a yield of 70.4% (0.200 g) of the title compound as a white solid, m.p. 91.5°–93.5° C.

B. Alternatively, to 150 ml of heated ethyl acetate in a Parr hydrogenation bottle was added 2.00 g (4.77 mmoles) of the compound produced in Example 6, Part A and 1.0 g of Lindlar's catalyst. The mixture was hydrogenated at 20 psi for 6 hours which yielded incomplete hydrogenation. Then, 0.5 g of Lindlar's catalyst was added three times over the next few hours. The reaction mixture was shaken for about 2½ days. Then, the reaction mixture was suction filtered through a Celite ® (Johns Mansville Corp.) pad with hot ethyl acetate followed by evaporation of the solvent in vacuo, column chromatographed on silica gel (90% ethyl acetate/hexanes, 1% triethylamine) and recrystallized from 1.5:1.0 hexanes/benzene to give a yield of 66.2% (1.33 g) of the title compound of this Example as a white solid, m.p. 93.5°–96.0° C.

C. Using the above procedure and starting with 1.96 g (4.68 mmoles) of the compound produced in Example 6, Part A and 1.5 g of Lindlar's catalyst gave a yield after recrystallization from 2:1 hexanes/benzene and air-drying of 84.3% (1.66 g) of the title compound of this Example as a beige solid, m.p. 94°–96° C.

EXAMPLE 9

Ethyl 1-ethyl-6,8-fluoro-7-(3-hydroxy-1-propenyl)-1,4-dihydroquinol-4-one 3-carboxylate To 20–25 ml of absolute ethanol was added 0.80 g (1.90 mmoles) of ethyl 1-ethyl-6,8-difluoro-7-(2-propen-1-tetrahydropyranyl-ol-3-yl)-1,4-dihydroquinol-4-one 3-carboxylate (Example 8, Part C) and a few crystals of p-toluene sulfonic acid monohydrate. The mixture was refluxed for 2 hours. Then the reflux condenser was removed and the ethanol allowed to evaporate to leave a small volume reaction mixture which was stored in a refrigerator overnight. The resulting precipitate was suction filtered with ether and hexane washes to give a yield of 91.3% (0.584 g) of the title compound as a white, crystalline solid, m.p. 162°–166° C.

EXAMPLE 10

Ethyl 1-cyclopropyl-6-fluoro-7-vinyl-1,4-dihydroquinol-4-one 3-carboxylate

A. Into a flame-dried, nitrogen purged flask was placed 0.86 ml (0.856 mmoles) of 1M vinyl magnesium bromide which was then cooled to −78° C. under nitrogen. Then, a solution containing 0.16 g (1.14 mmoles) of fused $ZnCl_2$ in 3–5 ml of anhydrous tetrahydrofuran was added. The resulting suspension was warmed to −20° C. and, sequentially, 0.101 g (0.285 mmoles) of ethyl 1-cyclopropyl-6-fluoro-7-bromo-1,4-dihydroquinol-4-one 3-carboxylate (Preparation D) in 13 ml of anhydrous tetrahydrofuran and 0.033 g (10 mole %) of tetrakis(triphenylphosphine)palladium were added. The reaction was warmed to room temperature and stirred overnight. The reaction was quenched by pouring the mixture into a separatory funnel containing ethyl acetate/saturated ammonium chloride. The organic phase was washed three times with saturated ammonium chloride, then once with brine, dried over anhydrous sodium sulfate, suction filtered and concentrated by evaporation in vacuo. The concentrate was column chromatographed on silica gel (95% ethyl acetate/hexanes) to give a yield of 43% (0.037 g) of the title compound of this Example as a yellow, fluorescent product.

B. The above procedure was repeated using 1.79 ml (1.79 mmoles) of 1M vinyl magnesium bromide, 0.333 g (2.44 mmoles) of fused $ZnCl_2$ in 10 ml of anhydrous tetrahydrofuran, 0.210 g (0.593 mmoles) of ethyl 1-cyclopropyl-6-fluoro-7-bromo-1,4-dihydroquinol-4-one 3-carboxylate in 26 ml of anhydrous tetrahydrofuran and 0.069 g (10 mole %) of tetrakis(triphenylphosphine)palladium. The reaction was run for 4 hours. Then, the product from Part A, above, was combined with the product from this Part B and recrystallized from benzene with added diethyl ether (Darco Treatment) to give 0.067 g of the title compound of this Example as light yellow crystals, m.p. 214°–217° C.

C. The procedure of Part A was repeated again using 2.37 ml (2.37 mmoles) of 1M vinyl magnesium bromide, 0.431 g (3.16 mmoles) of fused $ZnCl_2$ in 25 ml of anhydrous tetrahydrofuran, 0.280 g (0.791 mmoles) of ethyl 1-cyclopropyl-6-fluoro-7-bromo-1,4-dihydroquinol-4-one 3-carboxylate in 25 ml of tetrahydrofuran, and 0.095 g (10 mole %) of tetrakis(triphenylphosphine)palladium. The reaction was run for 1.5 hours. Column chromatography on silica gel (90% ethyl acetate/hexanes, 1% triethylamine) resulted in a yield of 48.3% (0.115 g), after recrystallization from hot alcohol, of the title compound of this Example, m.p. 221°–223° C.

EXAMPLE 11

Ethyl 1-cyclopropyl-6-fluoro-7-cyclopropyl-1,4-dihydroquinoline-4-one 3-carboxylate To a mixture of cold 15 ml of 40% potassium hydroxide and 15 ml of ethyl acetate was added 0.76 g (5.15 mmoles) of N-methyl-N'-nitro-N-nitrosoguanidine to form a diazomethane solution. A separate mixture was prepared by adding 0.155 g (0.515 mmoles) of ethyl 1-cyclopropyl-6-fluoro-7-vinyl-1,4-dihydroquinol-4-one 3-carboxylate to 50 ml of 6:1 ethyl acetate/chloroform and then this mixture was cooled to 0° C. The yellow, organic diazomethane solution was added to the other reactants and several milligrams of palladium (II) acetate were added to the reaction mixture with evolution of nitrogen gas. Additional fresh diazomethane solutions were prepared as described starting after 2 hours of reaction time and a total of seven further additions of fresh diazomethane with additional palladium (II) acetate catalyst were made over a total reaction time of 9 hours. Then, the reaction mixture was poured into 1:1 ethyl acetate/deionized water and the organic layer was washed once with 1:1 acetic acid/deionized water, several times with saturated sodium bicarbonate solution and twice with brine. The organic layer was then dried over sodium sulfate, suction filtered, concentrated by evaporation in vacuo and column chromatographed on silica gel (80% ethyl acetate/hexanes, 1% triethylamine) to give a yield of 68.5% (0.111 g) of the title compound as a solid, m.p. 215°–218° C.

EXAMPLE 12

1-Cyclopropyl-6-fluoro-7-cyclopropyl-1,4-dihydroquinol-4-one 3-carboxylic acid

To a mixture of 7 ml of 1N hydrochloric acid and 7 ml of anhydrous tetrahydrofuran was added 0.105 g (0.333 mmoles) of ethyl 1-cyclopropyl-6-fluoro-7-cyclopropyl-1,4-dihydroquinol-4-one 3-carboxylate. The reaction mixture was stirred and heated in an oil bath at about 70° C. for 18 hours. Then, after evaporation of the tetrahydrofuran, the reaction mixture was cooled for several hours in a refrigerator. The resulting precipitate was recovered by suction filtration, air-dried and heated in an evacuated drying pistol (acetone) to give a yield of 73% (0.070 g) of the title compound as shiny, pale yellow crystals, m.p. 218°–220° C.

EXAMPLE 13

Ethyl 1-ethyl-6,8-difluoro-7-(3-azido-1-propenyl)-1,4-dihydroquinol-4-one 3-carboxylate A. Preparation of hydrazoic acid (Organic Reactions, Vol. III, page 327, John Wiley & Sons, Inc., New York).

To 3.25 ml of deionized water in a flask fitted with a thermometer and a gas outlet adapter was added 3.25 g (50 mmoles) of sodium azide and a magnetic stirrer. The reaction mixture was stirred and cooled to 0° C. Then, 30 ml of benzene was added followed by the addition of 2.45 g of concentrated sulfuric acid while maintaining the reaction mixture below 10° C. The organic layer was decanted and dried over anhydrous sodium sulfate at about 0° C.

B. According to the basic procedure described in Helvetica Chimica Acta, Vol. 59, Fasc. 6, pages 2100–2113 (1976), to 0.087 g (0.327 mmoles) of triphenylphosphine in 7.5 ml of benzene was added 0.100 g (0.297 mmoles) of ethyl 1-ethyl-6,8-difluoro-7-(3-hydroxy-1-propenyl)-1,4-dihydroquinol-4-one 3-carboxylate (Example 9) at room temperature. To this suspension was added approximately 3.5 ml of the benzene solution of hydrazoic acid (prepared in Part A, above) and 0.057 g (0.327 mmoles) of diethyl azodicarboxylate in 1.5 ml of benzene. After 0.5 hours, the reaction was quenched with saturated sodium bicarbonate solution. The organic layer was washed once with saturated brine, dried over anhydrous sodium sulfate, suction filtered and concentrated by evaporation in vacuo. The concentrate was column chromatographed on silica gel (70% ethyl acetate/hexanes, 1% triethylamine) to give a yield of 64.6% (0.0691 g) of the title compound of this Example as beige/white crystals, m.p. 106°–110° C.

EXAMPLE 14

Ethyl 1-ethyl-6,8-difluoro-7-(2-hydroxymethyl-1-cyclopropyl)-1,4-dihydroquinol-4-one 3-carboxylate A. To 30 ml of ethyl acetate was added 0.607 g (1.44 mmoles) of ethyl 1-ethyl-6,8-difluoro-7-(3-(tetrahydropyranyl)oxy-1-propenyl)-1,4-dihydroquinol-4-one 3-carboxylate and the mixture was cooled to 8° C. A separate mixture of 40-45 ml of ether and 30 ml of a 40% potassium hydroxide solution was prepared, cooled to 0° C. and then 4.24 g (28.8 mmoles) of N-methyl-N'-nitro-N-nitrosoguanidine was added to produce diazomethane. The ether/diazomethane solution was transferred to the reaction mixture above, and a small amount of palladium (II) acetate catalyst was added. Four additional diazomethane solutions were prepared as above and added to the reaction mixture with additional palladium (II) acetate catalyst over a total reaction time of 46 hours. The reaction mixture was suction filtered to remove the precipitated catalyst and the filtrate was added to ethyl acetate/dilute glacial acetic acid. The organic layer was washed several times with saturated sodium bicarbonate, dried over anhydrous sodium sulfate, suction filtered and concentrated by evaporation in vacuo. The concentrate was then chromatographed on silica gel (50→55% ethyl acetate/hexanes, 1% triethylamine) to give a yield of 48.8% (0.306 g) of a yellow oil after high vacuum removal of residual solvent.

B. To 10 ml of absolute alcohol was added 0.306 g (0.703 mmoles) of the product of Part A of this Example and a few crystals of p-toluenesulfonic acid monohydrate. The reaction mixture was refluxed for 6.5 hours and then concentrated by evaporation. The concentrate was cooled to room temperature, diluted with 75 ml of ethyl acetate, washed twice with saturated sodium bicarbonate and once with brine and dried over anhydrous sodium sulfate. Then, the solution was suction filtered, concentrated by evaporation in vacuo and subjected to high vacuum for removal of residual solvent to give a yield of 87.9% (0.217 g) of the title compound of this Example as a beige solid, m.p. 135°–138° C.

EXAMPLE 15

Ethyl 1-ethyl-6,8-difluoro-7-(2-azidomethyl-1-cyclopropyl)-1,4-dihydroquinol-4-one 3-carboxylate To 8 ml of benzene at room temperature was added 0.100 g (0.285 mmoles) of ethyl 1-ethyl-6,8-difluoro-7-(2-hydroxymethyl-1-cyclopropyl)-1,4-dihydroquinol-4-one 3-carboxylate (Example 14) and 0.112 g (0.427 mmoles) of triphenylphosphine. To this suspension was added a benzene solution of hydrazoic acid prepared according to the procedure in Part A of Example 13 and 0.074 g (0.427 mmoles) of diethyl azodicarboxylate in 1 ml of benzene. The reaction was stirred at room temperature overnight and then charged with 0.56 g (2.14 mmoles) of triphenylphosphine, fresh hydrazoic acid and 0.37 g (2.13 mmoles) of diethyl azodicarboxylate. After a further 0.5 hours the reaction was quenched with saturated sodium bicarbonate. The organic layer was washed once more with saturated sodium bicarbonate, once with saturated brine and then dried over anhydrous sodium sulfate. The mixture was then suction filtered, concentrated by evaporation in vacuo, column chromatographed on silica gel (75% ethyl acetate/hexanes, 1% triethylamine) and rechromatographed on silica gel (40% ethyl acetate/hexanes 1% triethylamine) to give a yield of 81.6% (0.087 g) of the title compound, High Resolution Mass Spec: Parent mol. ion at m/e 376, base peak m/e 304 (M-72).

EXAMPLE 16

1-Ethyl-6,8-difluoro-7-(2-hydroxymethyl-1-cyclopropyl)-1,4-dihydroquinol-4-one 3-carboxylic acid To a mixture of 7 ml of tetrahydrofuran and 7 ml of 1N hydrochloric acid was added 0.0881 g (0.251 mmoles) of ethyl 1-ethyl-6,8-difluoro-7-(2-hydroxymethyl-1-cyclopropyl)-1,4-dihydroquinol-4-one 3-carboxylate (Example 14) and the reaction mixture was refluxed for 6 hours. The reflux condenser was removed and the tetrahydrofuran allowed to evaporate. The mixture was then stored overnight in a refrigerator in a corked vessel. The resulting white precipitate was recovered by suction filtration, washed several times with deionized water followed by diethyl ether and then air-dried to give a yield of 67.2% (0.0545 g) of the title compound as a white powder, m.p. 201°-203° C.

EXAMPLE 17

1-Ethyl-6,8-difluoro-7-(3-azido-1-propenyl)-1,4-dihydroquinol-4-one 3-carboxylic acid To a mixture of 2 ml of 1N hydrochloric acid and 3 ml of tetrahydrofuran was added 0.0583 g (0.161 mmoles) of ethyl 1-ethyl-6,8-difluoro-7-(3-azido-1-propenyl)-1,4-dihydroquinol-4-one 3-carboxylate (Example 13) and the reaction mixture was refluxed for 22.5 hours. Then, the tetrahydrofuran was removed by evaporation and the mixture cooled to room temperature. The resulting white precipitate was recovered by suction filtration and air-dried to give a yield of 79% (0.0425 g) of the title compound as a white solid, m.p. ~190° C.

EXAMPLE 18

Ethyl 1-ethyl-6,8-difluoro-7-(2-methylamino-1-cyclopropyl)-1,4-dihydroquinol-4-one-3-carboxylate Using the procedure of Example 8, part A, the title compound is prepared by hydrogenation of the compound of Example 15.

EXAMPLE 19

Employing the procedure described in Example 17, the following carboxylic acids ($R_1$ =H) are prepared from the corresponding esters.

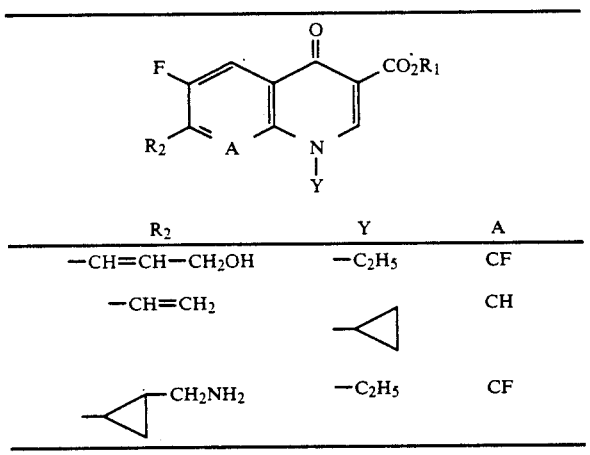

| $R_2$ | Y | A |
|---|---|---|
| —CH=CH—CH$_2$OH | —C$_2$H$_5$ | CF |
| —CH=CH$_2$ | ◁ | CH |
| ◁—CH$_2$NH$_2$ | —C$_2$H$_5$ | CF |

PREPARATION A

Ethyl 1-ethyl-6,8-difluoro-7-bromo-1,4-dihydroquinol-4-one 3-carboxylate

The title compound of this Preparation is prepared according to the method described in Example 1 of U.S. Pat. No. 4,623,650 to Gilligan et al., the teachings of which are incorporated herein by reference.

PREPARATION B

N-cyclopropyl-3-bromo-4-fluoroaniline

To a flame dried flask containing 60 ml of anhydrous ethyl ether was added 5.63 g (46.5 mmoles) of cyclopropylbromide, and then the mixture was cooled to −78° C. under a nitrogen atmosphere. Then, 27.4 ml (46.5 mmoles) of 1.7M t-butyllithium was added slowly. The mixture was then warmed to −40° C. Into another flame dried flask was placed 2.95 g (15.5 mmoles) of 3-bromo-4-fluoroaniline and 50 ml of anhydrous tetrahydrofuran. This mixture was also cooled to -78° C. under nitrogen atmosphere. Then, 9.7 ml (15.5 mmoles) of 1.6M n-butyllithium was added to the second mixture which was stirred at −78° C. for 25 minutes followed by the addition of 1.39 g (15.5 mmoles) of cuprous cyanide. The mixture was then warmed to −40° C., stirred for 30 minutes at −40° C. and then cooled to −78° C. Then, the anilinocuprate was added via inverse addition by a cannula to the cyclopropyllithium/ether solution at −78° C. The reaction mixture was warmed to room temperature and maintained at room temperature overnight followed by heating to 35° C. in an oil bath for about 9 hours. The mixture was cooled to −78° C., oxygen was added for 5 minutes and then 100 ml of 1:1 concentrated ammonium hydroxide/saturated ammonium chloride was added. The mixture was warmed to room temperature, and the organic layer was washed three times with 1:1 ammonium hydroxide/ammonium chloride and twice with saturated brine. The resulting solution was dried over anhydrous sodium sulfate, suction filtered, concentrated in vacuo and column chromatographed on silica gel (20% ethyl acetate/hexanes, 1% triethylamine) to give the title compound as two components [1.03 g (28.9% yield) and 1.30 g (44.1%) yield].

PREPARATION C

Diethyl-3-bromo-4-fluoro-N-cyclopropylanilinomethylene malonate

To 0.89 g (4.13 mmoles) diethyl ethoxymethylene malonate was added 0.95 g (4.13 mmoles) of N-cyclopropyl-3-bromo-4-fluoroaniline prepared according to Preparation B. The mixture was heated to 150°-160° C. under a nitrogen atmosphere. After 1.5 hours some starting material remained so additional diethyl ethoxymethylene malonate was added to the reaction mixture which was heated at 150°-160° C. overnight for a total reaction time of 18 hours. The mixture was column chromatographed on silica gel (5% ethyl acetate/hexanes, 1% triethylamine) to give a yield of 90.9% (1.5 g) of an oil containing the title compound of this Preparation.

The above procedure was repeated using 0.69 g (3.0 mmoles) of N-cyclopropyl-3-bromo-4-fluoroaniline and 0.65 g (3.0 mmoles) of diethyl ethoxymethylene malonate for a reaction time of 4 hours which, after column chromatography on silica gel (1-15% ethyl acetate/hexanes, 1% triethylamine) gave a yield of 55% (0.66 g) of a brown oil containing the title compound of this Preparation.

PREPARATION D

Ethyl 1-cyclopropyl-6-fluoro-7-bromo-1,4-dihydroquinol-4-one 3-carboxylate

To 14 ml of PPE at 150° C. was slowly added 2.14 g (5.35 mmoles) of the compound produced in Preparation C in about 72 ml of ether. The ether was allowed to evaporate and the contents stirred for 60 minutes under a nitrogen atmosphere at 150° C. The reaction was cooled to room temperature and quenched with deionized water. The resulting suspension was slowly neutralized with saturated sodium bicarbonate and then stirred for 3 hours. After ascertaining that the pH had remained neutral, the precipitate was recovered by suction filtration, washed with deionized water and partially air-dried. The resulting solid was dissolved in 1:1 ethyl acetate/methylene chloride, washed three times with deionized water, washed twice with saturated brine and then dried over anhydrous sodium sulfate. The solution was then suction filtered, concentrated by evaporation in vacuo and column chromatographed on silica gel (75% ethyl acetate/hexanes, 1% triethylamine) to give a yield of 13% (0.10 g) of the title compound of this Preparation and 28% (0.21 g) of the opposite regioisomer of the title compound.

PREPARATION E

Ethyl 1-ethyl-6-fluoro-7-bromo-1,4-dihydroquinol-4-one 3-carboxylate

To 85 ml of anhydrous dimethylformamide were added 6.05 g (19.3 mmoles) of 7-bromo-6-fluoroquinolone ethyl ester, 6.06 g (38.5 mmoles) of ethyl iodide and 8.0 g (57.9 mmoles) of anhydrous potassium carbonate under a nitrogen atmosphere. The reaction mixture was heated to 50° C. overnight. The reaction mixture was poured into a separatory funnel containing ethyl acetate/deionized water. The organic layer was then extracted three times with deionized water, once with saturated brine and then dried over anhydrous sodium sulfate. Then, the solution was suction filtered, concentrated by evaporation in vacuo and column chromatographed on silica gel (70% ethyl acetate/hexanes, 1% triethylamine) to give three separate products. The desired compound of this Preparation was thus obtained by chromatography giving a yield of 69.5% (4.85 g) as a white solid.

What is claimed is:

1. A compound of the formula

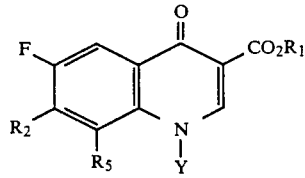

wherein $R_5$ is H, F, Cl or $OCH_3$;

$R_1$ is H, $(C_1-C_7)$alkyl, benzyl or a pharmaceutically acceptable cation;

$R_2$ is vinyl, W substituted vinyl, $CH_3C\equiv C-$; $W-CH_2C\equiv C-$, cyclopropyl or

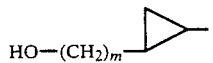

W is $R_3-(CH_2)_m$; m is 1 or 2; $R_3$ is OH, $NH_2$, $NH(C_1-C_3)$alkyl, $SO_2(C_1-C_3)$alkyl, $SO_2NH(C_1-C_3)$alkyl or $SO_2NH_2$; Y is $(C_1-C_3)$alkyl, $(C_1-C_3)$haloalkyl, cyclopropyl, vinyl, p-fluorophenyl, o,p-difluorophenyl or a pharmaceutically-acceptable salt thereof, provided that when $R_5$ is H and Y is $(C_1-C_3)$alkyl or cyclopropyl, $R_2$ is not cyclopropyl.

2. A compound according to claim 1 wherein $R_5$ is H or R.

3. A compound according to claim 1 wherein $R_2$ is cyclopropyl.

4. A compound according to claim 1 wherein $R_2$ and Y are each cyclopropyl.

5. A compound according to claim 4 wherein $R_5$ is F.

6. A compound according to claim 1 wherein $R_1$ is H.

7. An antibacterial composition comprising an antibacterially effective amount of a compound according to claim 1 or a pharmaceutically acceptable salt thereof and a pharmaceutically acceptable carrier.

8. A method of treating a host affected by bacterial disease which comprises administering to said host an antibacterially effective amount of a compound according to claim 1 or a pharmaceutically acceptable salt thereof.

* * * * *

UNITED STATES PATENT AND TRADEMARK OFFICE
CERTIFICATE OF CORRECTION

PATENT NO. : 5,039,682
DATED : August 13, 1991
INVENTOR(S) : Paul R. McGuirk

It is certified that error appears in the above-identified patent and that said Letters Patent is hereby corrected as shown below:

Column 13, line 36, "NCH" should read -- $NCH_3$ --;

Column 24, line 67, "ml of hexanes" should read -- 6 ml of hexanes --; and

Claim 2, column 32, line 30, "R" should read -- F --.

Signed and Sealed this

Fourth Day of January, 1994

Attest:

BRUCE LEHMAN

Attesting Officer  Commissioner of Patents and Trademarks